United States Patent
Kast et al.

(10) Patent No.: US 9,008,782 B2
(45) Date of Patent: Apr. 14, 2015

(54) OCCIPITAL NERVE STIMULATION

(75) Inventors: John E. Kast, Hugo, MN (US); William Witt, Lexington, KY (US)

(73) Assignee: Medtronic, Inc., Minneapolis, MN (US)

( * ) Notice: Subject to any disclaimer, the term of this patent is extended or adjusted under 35 U.S.C. 154(b) by 1541 days.

(21) Appl. No.: 12/183,214

(22) Filed: Jul. 31, 2008

(65) Prior Publication Data
US 2009/0112282 A1    Apr. 30, 2009

Related U.S. Application Data

(60) Provisional application No. 61/000,533, filed on Oct. 26, 2007.

(51) Int. Cl.
*A61N 1/375*   (2006.01)
*A61N 1/05*    (2006.01)
*A61N 1/36*    (2006.01)

(52) U.S. Cl.
CPC .............. *A61N 1/375* (2013.01); *A61N 1/0553* (2013.01); *A61N 1/0558* (2013.01); *A61N 1/36071* (2013.01); *A61N 1/3752* (2013.01); *A61N 1/3758* (2013.01)

(58) Field of Classification Search
CPC .............................. A61N 1/375; A61N 1/3752
USPC ....................................................... 607/36, 46
See application file for complete search history.

(56) References Cited

U.S. PATENT DOCUMENTS

| | | | |
|---|---|---|---|
| 4,207,903 A | 6/1980 | O'Neill | |
| 4,254,776 A | 3/1981 | Tanie et al. | |
| 4,467,817 A | 8/1984 | Harris | |
| 4,509,521 A | 4/1985 | Barry | |
| 4,627,438 A | 12/1986 | Liss et al. | |
| 4,646,755 A | 3/1987 | Kane | |
| 4,856,526 A | 8/1989 | Liss et al. | |

(Continued)

FOREIGN PATENT DOCUMENTS

| | | |
|---|---|---|
| WO | WO 03/033068 | 4/2003 |
| WO | WO 2006/098823 | 9/2006 |

(Continued)

OTHER PUBLICATIONS

"Medtronic Neurostimulation System for the Treatment of Chronic Migraine Headache," System Manual, Medtronic, Inc., 2006 (47 pgs.).

(Continued)

*Primary Examiner* — Eric D. Bertram
(74) *Attorney, Agent, or Firm* — Shumaker & Sieffert, P.A.

(57) ABSTRACT

An implantable medical device comprises one or more electrical stimulation generators, and a housing that contains the one or more electrical stimulation generators. The implantable medical device also includes a first medical lead no greater than about 6 inches in length, and a second medical lead no greater than about 6 inches in length. The housing includes a first connector block that electrically connects the first medical lead to at least one of the one or more electrical stimulation generators, and a second connector block that electrically connects the second medical lead to at least one of the one or more electrical stimulation generators. The implantable medical device may be part of an electrical stimulation system implanted beneath the skin and inferior to the inion of a patient to deliver stimulation therapy to at least one of an occipital nerve and a branch of the occipital nerve.

29 Claims, 8 Drawing Sheets

(56) References Cited

U.S. PATENT DOCUMENTS

| | | |
|---|---|---|
| 4,972,847 A | 11/1990 | Dutcher et al. |
| 5,003,990 A | 4/1991 | Osypka |
| 5,143,067 A | 9/1992 | Rise et al. |
| 5,193,539 A | 3/1993 | Schulman et al. |
| 5,215,086 A | 6/1993 | Terry, Jr. et al. |
| 5,388,578 A | 2/1995 | Yomtov et al. |
| 5,411,538 A * | 5/1995 | Lin .................................. 607/33 |
| 5,443,492 A | 8/1995 | Stokes et al. |
| 5,447,521 A | 9/1995 | Anderson et al. |
| 5,540,734 A | 7/1996 | Zabara |
| 5,562,718 A | 10/1996 | Palermo |
| 5,578,060 A | 11/1996 | Pohl et al. |
| 5,645,586 A | 7/1997 | Meltzer |
| 5,653,739 A | 8/1997 | Maurer et al. |
| 5,895,414 A | 4/1999 | Sanchez-Zambrano |
| 5,961,542 A | 10/1999 | Agarwala |
| 5,987,352 A | 11/1999 | Klein et al. |
| 6,016,449 A | 1/2000 | Fischell et al. |
| 6,041,259 A | 3/2000 | Agarwala et al. |
| 6,052,624 A | 4/2000 | Mann |
| 6,061,593 A | 5/2000 | Fischell et al. |
| 6,128,538 A | 10/2000 | Fischell et al. |
| 6,134,474 A | 10/2000 | Fischell et al. |
| 6,176,879 B1 | 1/2001 | Reischl et al. |
| 6,249,707 B1 | 6/2001 | Kohnen et al. |
| 6,269,266 B1 | 7/2001 | Leysieffer |
| 6,301,500 B1 | 10/2001 | Van Herk et al. |
| 6,308,105 B1 | 10/2001 | Duysens et al. |
| 6,327,502 B1 | 12/2001 | Johansson et al. |
| 6,356,788 B2 | 3/2002 | Boveja |
| 6,360,122 B1 | 3/2002 | Fischell et al. |
| 6,366,814 B1 | 4/2002 | Boveja et al. |
| 6,381,496 B1 | 4/2002 | Meadows et al. |
| 6,445,955 B1 | 9/2002 | Michelson et al. |
| 6,473,653 B1 | 10/2002 | Schallhorn et al. |
| 6,505,075 B1 | 1/2003 | Weiner |
| 6,526,318 B1 | 2/2003 | Ansarinia |
| 6,622,048 B1 | 9/2003 | Mann et al. |
| 6,647,292 B1 | 11/2003 | Bardy et al. |
| 6,647,296 B2 | 11/2003 | Fischell et al. |
| 6,658,302 B1 | 12/2003 | Kuzma et al. |
| 6,662,051 B1 | 12/2003 | Eraker et al. |
| 6,735,475 B1 | 5/2004 | Whitehurst et al. |
| 6,847,849 B2 | 1/2005 | Mamo et al. |
| 6,944,503 B2 | 9/2005 | Crowe et al. |
| 6,999,819 B2 | 2/2006 | Swoyer et al. |
| 7,092,765 B2 | 8/2006 | Geske et al. |
| 7,103,415 B2 | 9/2006 | Probst et al. |
| 7,218,964 B2 | 5/2007 | Hill et al. |
| 7,231,252 B2 | 6/2007 | Duncan et al. |
| 7,231,256 B2 | 6/2007 | Wahlstrand et al. |
| 7,299,093 B2 | 11/2007 | Zhu et al. |
| 7,515,964 B1 * | 4/2009 | Alexander et al. .............. 607/38 |
| 7,711,419 B2 * | 5/2010 | Armstrong et al. ............... 607/2 |
| 2001/0003799 A1 | 6/2001 | Boveja |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0099412 A1 | 7/2002 | Fischell et al. |
| 2002/0138116 A1 | 9/2002 | Bertolucci |
| 2002/0147485 A1 | 10/2002 | Mamo et al. |
| 2002/0161403 A1 | 10/2002 | Meadows et al. |
| 2002/0198572 A1 | 12/2002 | Weiner |
| 2003/0004428 A1 | 1/2003 | Pless et al. |
| 2003/0097161 A1 | 5/2003 | Firlik et al. |
| 2003/0114905 A1 | 6/2003 | Kuzma |
| 2003/0208248 A1 | 11/2003 | Carter et al. |
| 2004/0002635 A1 | 1/2004 | Hargrove et al. |
| 2004/0054297 A1 | 3/2004 | Wingeier et al. |
| 2004/0054388 A1 | 3/2004 | Osypka |
| 2004/0064158 A1 | 4/2004 | Klein et al. |
| 2004/0172089 A1 | 9/2004 | Whitehurst et al. |
| 2004/0193229 A1 * | 9/2004 | Starkebaum et al. ........... 607/40 |
| 2004/0215288 A1 | 10/2004 | Lee et al. |
| 2005/0033393 A1 | 2/2005 | Daglow |
| 2005/0043765 A1 | 2/2005 | Williams et al. |
| 2006/0036307 A1 | 2/2006 | Zarembo et al. |
| 2006/0206162 A1 | 9/2006 | Wahlstrand et al. |
| 2006/0206163 A1 | 9/2006 | Wahlstrand et al. |
| 2006/0206165 A1 | 9/2006 | Jaax et al. |
| 2007/0162087 A1 | 7/2007 | Wahlstrand et al. |
| 2007/0179581 A1 | 8/2007 | Dennis et al. |
| 2007/0208391 A1 | 9/2007 | Wahlstrand et al. |
| 2007/0255379 A1 | 11/2007 | Williams et al. |
| 2008/0046056 A1 | 2/2008 | O'Connor |
| 2008/0132979 A1 | 6/2008 | Gerber |

FOREIGN PATENT DOCUMENTS

| | | |
|---|---|---|
| WO | WO 2006/098824 | 9/2006 |
| WO | WO2008/066557 A1 | 6/2008 |

OTHER PUBLICATIONS

Office action for U.S. Appl. No. 12/183,224, dated Mar. 22, 2012, 13 pages.

* cited by examiner

OCCIPITAL NERVE STIMULATION

This application claims the benefit of U.S. Provisional Application No. 61/000,533, filed Oct. 26, 2007, the entire content of which is incorporated herein by reference.

TECHNICAL FIELD

The present disclosure relates to implantable medical devices, and more particularly, to implantable medical devices for delivery of electrical stimulation therapy.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals.

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by delivering electrical stimulation therapy to the occipital region via an implanted stimulation lead.

SUMMARY

This disclosure includes techniques for implanting an electrical stimulation system including a housing with a stimulation generator and electrical stimulation leads inferior to the inion of a patient. The disclosed techniques may be used to treat alleviate occipital neuralgia.

In one embodiment, an implantable medical device comprises one or more electrical stimulation generators, and a housing that contains the one or more electrical stimulation generators. The implantable medical device also includes a first medical lead no greater than about 6 inches in length, and a second medical lead no greater than about 6 inches in length. The housing includes a first connector block that electrically connects the first medical lead to at least one of the one or more electrical stimulation generators, and a second connector block that electrically connects the second medical lead to at least one of the one or more electrical stimulation generators.

In another embodiment, an electrical stimulation system comprises an electrical stimulator. The electrical stimulator comprises a housing having a width and a length that are each greater than a thickness of the housing, one or more stimulation generators within the housing, and at least two connector blocks. Each connector block accepts a medical lead. The electrical stimulation system further comprises at least two medical leads extending from the housing and electrically coupled to the stimulation generator via the connector blocks. Two of the medical leads connect to the housing at separate locations, wherein the separate locations are separated by at least a third of the length of the housing, wherein each of the at least two medical leads are no greater than about 6 inches in length.

In another embodiment, a method for implanting an electrical stimulation system in a patient comprises making an incision in the skin of a patient inferior to the inion of the patient. The paths are sized to accept medical leads of the electrical stimulation system. The method further includes forming an inferior pocket under the skin inferior to the inion, wherein the pocket is sized to accept a housing of an electrical stimulator of the electrical stimulation system, inserting the medical leads of the electrical stimulation system into the lateral paths, inserting the housing into the inferior pocket and closing the incision.

The details of one or more aspects of the present disclosure are set forth in the accompanying drawings and the description below. Other features, objects, and advantages of the disclosed techniques will be apparent from the description and drawings, and from the claims.

DETAILED DESCRIPTION

In general, the disclosure is directed to techniques for delivering electrical stimulation therapy to an occipital region of a patient via an implanted stimulation device. An electrical stimulator, once implanted, provides stimulation site treatment of head, neck, or facial pain or tension, including pain or tension caused by occipital neuralgia. The stimulation site may generally reside within the upper cervical region of the spine, e.g., C1-C4, and may target occipital nerves and branches in that region. For example, targeted nerves may include trigeminal nerves, greater occipital nerves, lesser occipital nerves, third occipital nerves and suboccipital nerves. An electrical stimulator can be implanted at the selected stimulation site adjacent a neuralgic region of the patient, and deliver neurostimulation therapy to treat pain and tension symptoms.

Figure 1A:
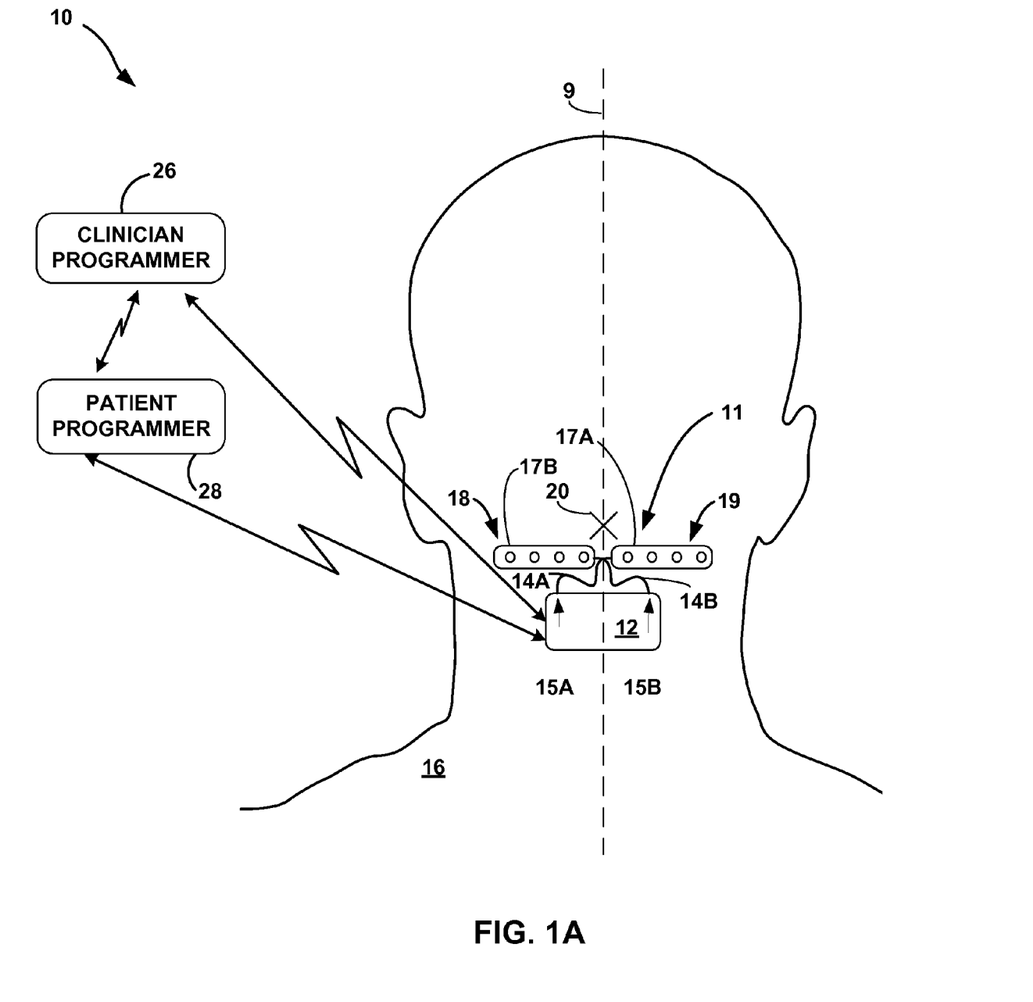
FIG. 1A is a schematic diagram of a therapy system, which includes an electrical stimulator coupled to two stimulation leads that have been implanted in a body of a patient for occipital nerve stimulation.
Figure 1B:
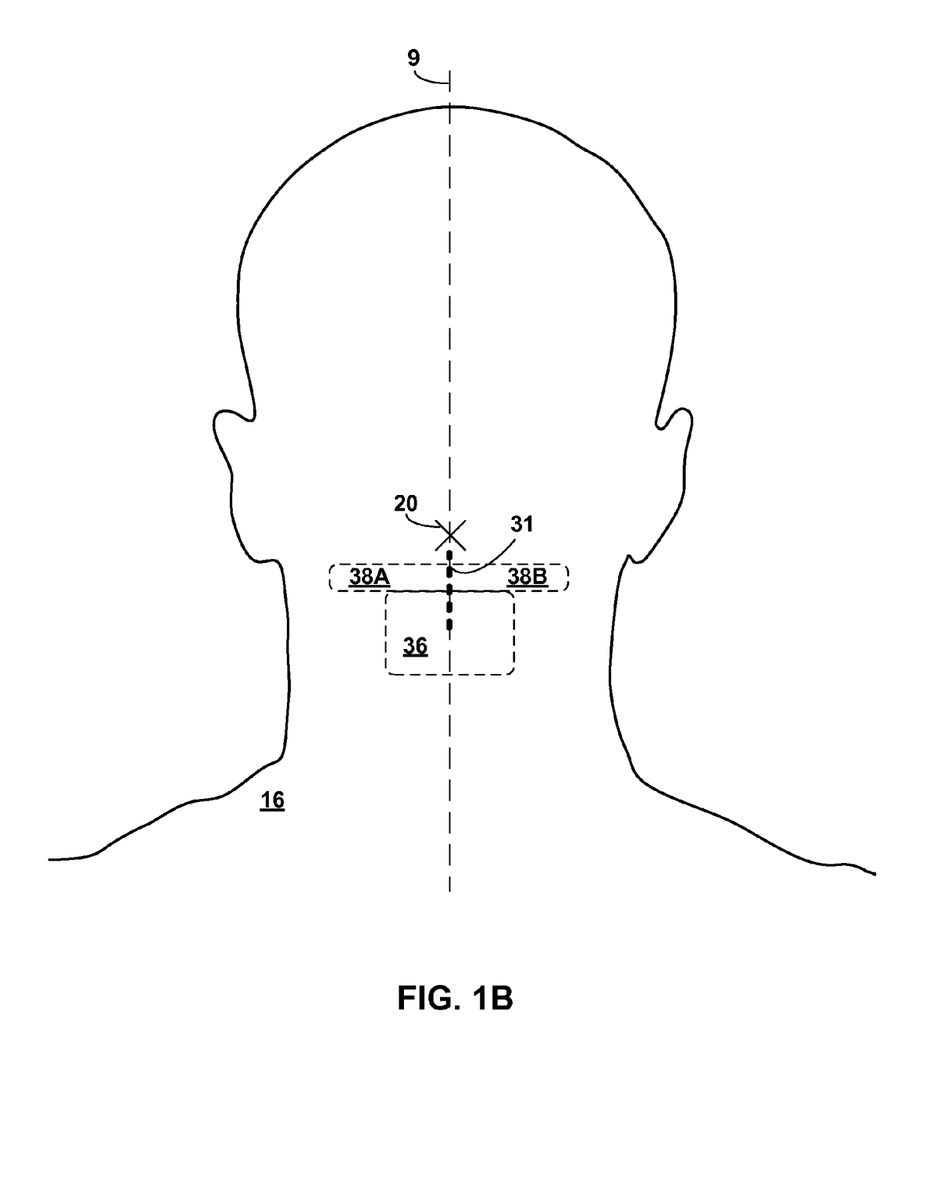
FIG. 1B illustrates a patient prior to implantation of the therapy system of FIG. 1A.
Figure 1C:
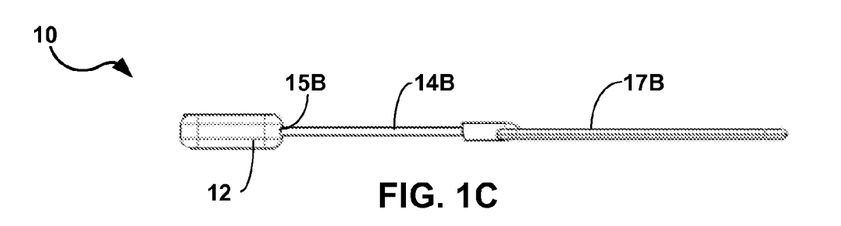
FIGS. 1C-1E illustrate the therapy system of FIG. 1A prior to implantation within the patient.
Figure 1D:
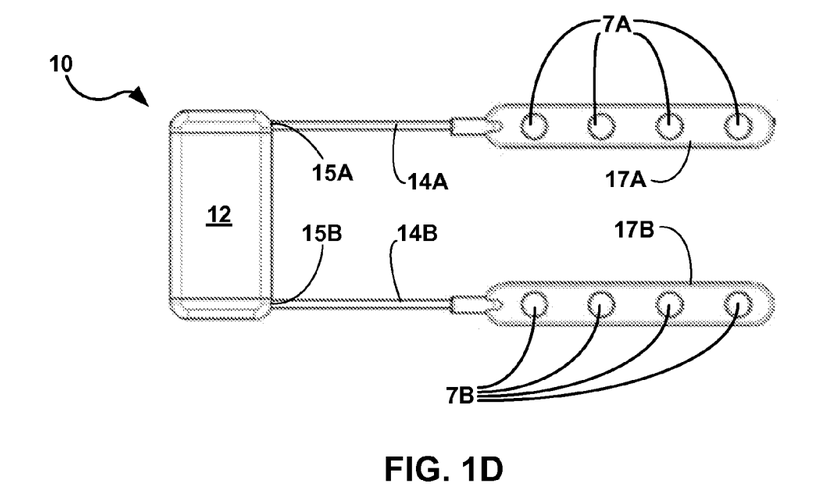
Figure 1E:
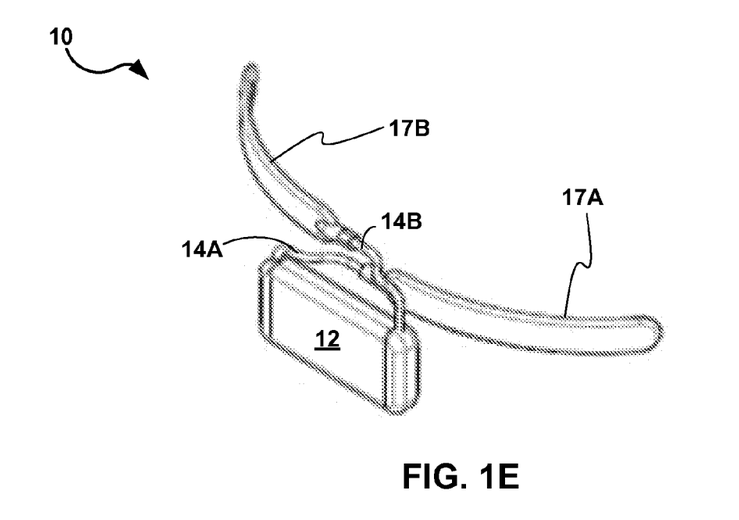

FIG. 1A is a schematic diagram of therapy system 10, which includes an electrical stimulator 12 coupled to stimulation leads 14A, 14B (collectively referred to as "leads 14"). In the example of FIG. 1A, electrical stimulator 12 is implanted in a human patient 16 proximate to an occipital region 11 within patient 16, below inion 20, the craniometric point that is the most prominent point at the occipital protuberance on the back of the head of patient 16. In the example of FIG. 1A, FIG. 1B illustrates patient 16 prior to implantation of therapy system 10, and FIGS. 1C-1E illustrate the therapy system 10 prior to implantation within patient 16.

Paddles 17A, 17B (collectively referred to as "paddles 17") include electrode sets 7A, 7B (collectively referred to as "electrodes 7") to deliver stimulation therapy to a therapy region, which generally encompasses occipital nerve sites and trigeminal nerve sites of patient 16. Such nerve sites may include, for example, an occipital nerve (e.g., a greater occipital nerve, lesser occipital nerve, third occipital nerve and suboccipital nerves), a trigeminal nerve, tissue adjacent to the trigeminal or occipital nerves, or a nerve branching from the occipital and/or trigeminal nerves. Thus, reference to an "occipital nerve" or a "trigeminal nerve" throughout the disclosure also may include branches of the occipital and trigeminal nerves, respectively. In addition, the stimulation therapy may be delivered to both an occipital nerve and trigeminal nerve by a single therapy system 10. While electrode sets 7 are linear in the example of FIG. 1D, other examples may utilize paddle electrodes including a two-dimensional array of electrodes. In other embodiments, axial leads with ring electrodes, segmented electrodes, or other electrodes may be used. Other lead and/or electrode configurations may be used.

Electrical stimulator 12 generates a stimulation signal (e.g., in the form of electrical pulses or substantially continuous waveforms). The stimulation signal may be defined by a variety of programmable parameters such as electrode combination, electrode polarity, stimulation voltage amplitude, stimulation current amplitude, stimulation waveform, stimulation pulse width, stimulation pulse frequency, etc.) that is delivered to occipital region 11 by implantable stimulation leads 14, respectively, and more particularly, via stimulation electrodes carried by stimulation leads 14. Electrical stimulator 12 may also be referred to as a pulse or signal generator, or a neurostimulator. In some embodiments, leads 14 may also carry one or more sense electrodes to permit electrical stimulator 12 to sense electrical signals or other sensors to sense other types of physiological parameters (e.g., pressure, activity, temperature, or the like) from occipital region 11, respectively. In some implementations, for example, such sensed parameters may be recorded for later analysis, e.g., evaluation of stimulation efficacy, or used in the control of stimulation therapy or therapy parameters.

The proximal ends of leads 14 are both electrically and mechanically coupled to separate connection ports 15A, 15B (collectively referred to as "ports 15") of electrical stimulator 12. Connection ports 15 are each located in a separate connector block within the housing of electrical stimulator 12. The connector blocks including connection ports 15 include terminals at different axial positions within the connector block that mate with contacts at different axial positions at proximal ends of leads 14. The connection between leads 14 and connection ports 15 also includes fluid seals to prevent undesirable electrical discharge. In different embodiments, leads 14 may be removed from connection ports 15 by a clinician if desired. For example, the removable connection may be a pressure, friction, or snap-fit, e.g., with a spring contacts. In other embodiments, leads 14 may be fixed to connection ports 15 such that simply pulling on leads 14 will not ordinarily release them from connection ports 15. Examples of relatively fixed connections include solder connections, set screws or other techniques.

In any event, conductors disposed in the lead body of each of leads 14 electrically connect stimulation electrodes (and sense electrodes, if present) adjacent to the distal ends of leads 14 to electrical stimulator 12. Connection ports 15 are located at least approximately a third of the length of the housing of electrical stimulator 12 apart from each other. For example, if the length of the housing is X, connection ports 15 are located at least ⅓*X apart from one another. Length may generally refer to a transverse or horizontal dimension of the housing of stimulator 12 in the example of FIG. 1A.

In the example of therapy system 10 shown in FIG. 1A, target tissue sites 18 and 19 are located within the patient's head or neck (e.g., proximate to one or more occipital nerve) and on opposite sides of midline 9 of patient 16. Midline 9 is a schematic representation of the line that divides patient 16 into about equal and symmetrical left and right halves. Delivering therapy to two target tissue sites, such as sites 18 and 19, may be used to deliver therapy to two nerve branches that branch from the same nerve. Nerves may branch into left and right branches that extend to opposite sides of midline 9, and therapy is delivered to two nerve branches on opposite sides of midline 9 (such as at target tissue sites 18 and 19). Stimulation of two nerve branches on opposite sides of midline 9 may be referred to as bilateral stimulation. However, bilateral stimulation may also refer to stimulation of any two regions of patient 16 either sequentially or simultaneously. Delivering therapy after nerves branch, e.g., closer to the nerve endings, may allow more targeted therapy delivery with fewer side effects. Therapy may also be delivered unilaterally to sites 18, 19. For example, stimulation therapy may be delivered to site 18 by paddle 17B simultaneously or alternately with stimulation of site 19 by paddle 17A. In addition, therapy may be delivered using an electrode set including at least one electrode from both paddle 17A and 17B.

Stimulation of the occipital region 11 (i.e., in regions of patient 16 proximate to occipital nerves, a trigeminal nerve or other cranial sites) may help alleviate pain associated with, for example, chronic migraines, cervicogenic headaches, occipital neuralgia or trigeminal neuralgia.

Therapy system 10, however, may be useful in other neurostimulation applications. Thus, in alternate embodiments, target tissue sites 18 and 19 may be at locations proximate to any other suitable nerve in body of patient 16, which may be selected based on, for example, a therapy program selected for a particular patient. For example, in other embodiments, therapy system 10 may be used to deliver neurostimulation therapy to other areas of the nervous system, in which cases lead 14 would be implanted proximate to the respective nerve(s). As one example, leads 14 may be implanted proximate to other nerves and/or structures of the head and neck of patient 16. As another example, system 10 may be implanted at other locations in a patient and used for sacral stimulation, pelvic floor stimulation, peripheral nerve field stimulation, spinal cord stimulation, deep brain stimulation, gastric stimulation, or subcutaneous stimulation other than occipital stimulation.

Accurate lead placement may affect the success of occipital nerve stimulation. If lead 14 is located too deep, i.e., anterior, in the subcutaneous tissue, patient 16 may experience muscle contractions, grabbing sensations, or burning. Such problems may additionally occur if one of leads 14 migrates after implantation. However, because electrical stimulator 12 is located proximate to target tissue sites 18 and 19, leads may be less than approximately six inches in length, which may provide a low electrical resistance and improve the efficiency of therapy system 10. Additionally, the short length of leads 14 also limits the potential for lead migration because patient movement does not create a significant stress on leads 14. In some embodiments, leads 14 may include fixation elements such as tines.

Therapy system 10 also may include a clinician programmer 26 and a patient programmer 28. Clinician programmer 26 may be a handheld computing device that permits a clinician to program neurostimulation therapy for patient 16, e.g., using input keys and a display. For example, using clinician programmer 26, the clinician may specify stimulation parameters for use in delivery of electrical stimulation therapy. Clinician programmer 26 supports telemetry (e.g., radio frequency telemetry) with electrical stimulator 12 to download neurostimulation parameters and, optionally, upload operational or physiological data stored by electrical stimulator 12. In this manner, the clinician may periodically interrogate electrical stimulator 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and electrical stimulator 12. In this manner, patient programmer 28 provides patient 16 with an interface for control of neurostimulation therapy by electrical stimulator 12. For example, patient 16 may use patient programmer 28 to start, stop or adjust neurostimulation therapy. In particular, patient programmer 28 may permit patient 16 to adjust stimulation parameters such as duration, amplitude, current, waveform, pulse width and pulse rate, within an adjustment range specified by the clinician via clinician programmer 28, or select from a library of stored stimulation therapy programs.

Electrical stimulator 12, clinician programmer 26, and patient programmer 28 may communicate wireless communication, as shown in FIG. 1A. Clinician programmer 26 and patient programmer 28 may, for example, communicate via wireless communication with electrical stimulator 12 using RF telemetry techniques known in the art. Clinician programmer 26 and patient programmer 28 also may communicate with each other using any of a variety of local communication techniques, such as RF communication according to the 802.11 or Bluetooth specification sets, infrared communication, e.g., according to the IrDA standard, or other standard or proprietary telemetry protocols.

In other embodiments, programmers 26 and 28 may communicate via a wired connection, such as via a serial communication cable, or via exchange of removable media, such as magnetic or optical disks, or memory cards or sticks. Further, the clinician programmer 26 may communicate with patient programmer 28 via remote telemetry techniques known in the art, communicating via a local area network (LAN), wide area network (WAN), public switched telephone network (PSTN), or cellular telephone network, for example.

FIG. 1B illustrates techniques for implantation of the therapy system 10 of FIG. 1A by a surgeon, physician, clinician or other caregiver. First, a clinician shaves the back of patient 16's head to ensure hair stays out of the way during the implantation. Then, as illustrated in FIG. 1B, incision 31 is made in the skin scalp of patient 16 along midline 9 of patient 16 inferior to inion 20. For example, incision 31 may start about 1 cm (e.g., a finger width) below the inion in the scalp of the patient. After incision 31 is made, lateral paths 38A and 38B (collectively referred to as "lateral paths 38") are tunneled to both the left and the right of incision 31 for leads 14 (FIG. 1A). For example, lateral paths 38 may be formed using blunt dissection. Inferior pocket 36 is also made for electrical stimulator 12 immediately below pockets 38. The distal ends of leads 14 including paddles 17 are inserted into pockets 38. Electrical stimulator 12 is rotated 180 degrees to twist leads 14 as shown in FIG. 1A. This rotation takes up slack in leads 14 to allow leads 14 to lie flat against the skull of patient 16 after implantation. Next, electrical stimulator 12 is inserted into pocket 36 via incision 31 by the clinician. Incision 31 only needs to be large enough so that electrical stimulator 12 may fit through incision 31. Then, incision 31 is closed over the implanted leads 14 and electrical stimulator 12. For example, incision 31 may be closed using glue and a vertical mattress suture technique. Other techniques such as taping or stapling may also be used.

Optionally, the distal ends of leads 14 may be secured in place. For example, leads 14 may include tines or the distal ends of leads 14 may be secured directly with a suture. In addition the housing of electrical stimulator 12 may also be secured in place using a suture.

Alternatively, a lateral incision may be used instead of lateral paths 38. Other embodiments may comprise using a lateral incision with paddle leads or using a midline incision with leads including ring electrodes instead of paddle leads.

In all embodiments, fluoroscopy may be used to locate the leads adjacent the target sites during the implantation. Additionally, patient 16 may be located on his or her side during implantation, which would allow an anesthesiologist to see his or her face.

FIG. 1C illustrates a side view of therapy system 10 including leads 14 and electrical stimulator 12. FIG. 1D illustrates a top view of therapy system 10. FIG. 1E illustrates a perspective view of therapy system 10. The connector blocks associated with connector ports 15 are oriented in about the same direction such that the leads 14 connect to a common side of electrical stimulator 12. As shown in FIG. 1E, paddles 17 are flexible to conform to the curvature of the skull of a patient. Electrical stimulator 12 may include rounded corners and/or a curved major surface to facilitate implantation inferior to the inion of a patient. For example, such a configuration may reduce the likelihood of necrosis to a patient's scalp adjacent the implant site.

Figure 2:
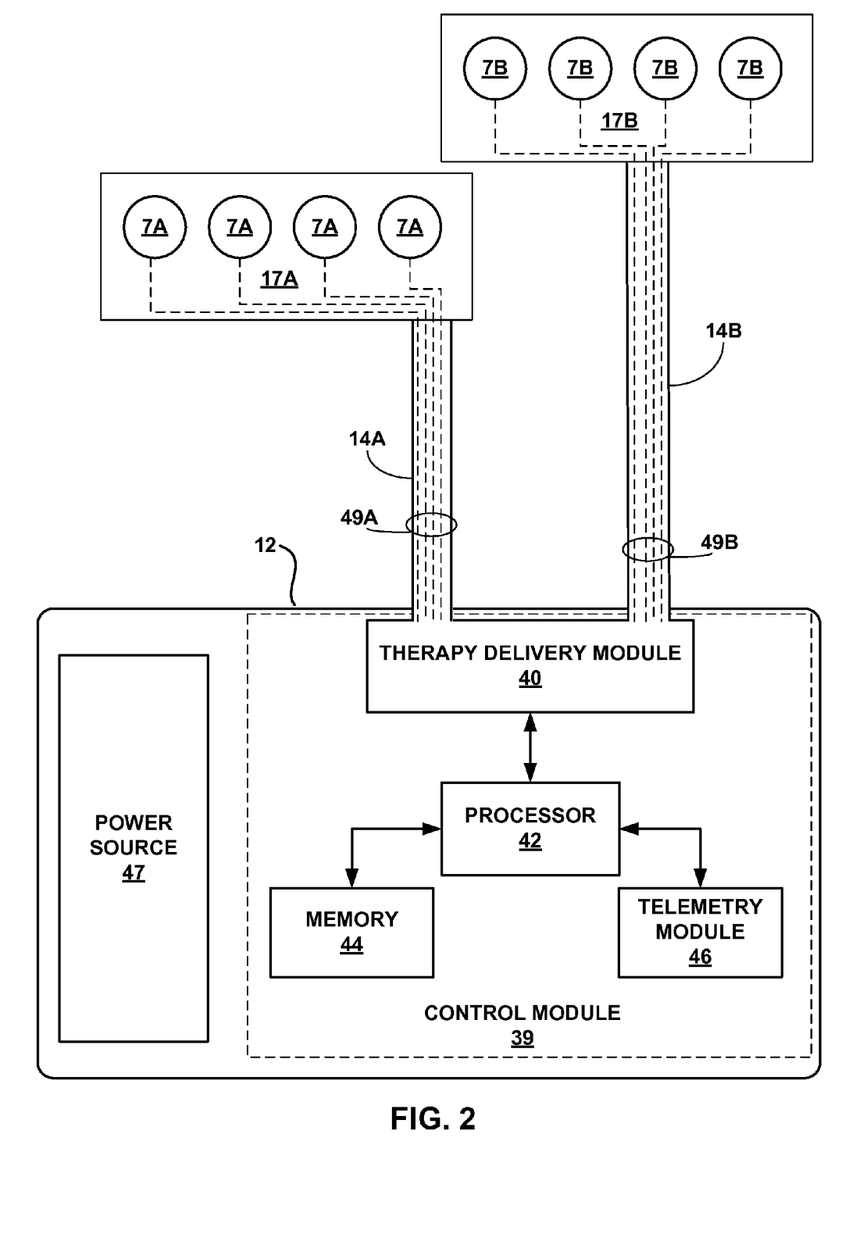
FIG. 2 is a block diagram illustrating various components of an electrical stimulator and medical leads of a therapy delivery system.

FIG. 2 is a block diagram illustrating a general example of various components of electrical stimulator 12 and medical leads 14. Electrical stimulator 12 may include power source 47 and control module 39 including therapy delivery module 40, processor 42, memory 44 and telemetry module 46. As one example, all or a portion of control module 39 may be implemented in an integrated circuit. In some embodiments, electrical stimulator 12 may also include a sensing circuit (not shown in FIG. 2). Medical paddle 17A includes electrodes 7A, which are each electrically coupled to therapy delivery module 40 via a separate conductor of conductor 49A of lead 14A. Likewise, medical paddle 17B includes electrodes 7B, which are each electrically coupled to therapy delivery module 40 via a separate conductor of conductor 49B of lead 14B. Conductors 49A and 49B are collectively referred to as conductors 49.

As one example, an implantable signal generator or other stimulation circuitry within therapy delivery module 40 delivers electrical signals (e.g., pulses or substantially continuous-time signals, such as sinusoidal signals) to targets stimulation sites 18 and 19 (FIG. 1) via selected combinations of at least some of electrodes 7 under the control of a processor 42. For example, electrical stimulator 12 may be configured to produce electrical pulses having one or more of the following attributes: a current amplitude between approximately 1 milliamps and 100 milliamps, a voltage amplitude between approximately 0.1 volts and 10 volts, a pulse frequency between approximately 10 Hz and 800 Hz and/or a pulse width between approximately 20 microseconds and 800 microseconds.

The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power. In addition to a rechargeable battery, in some cases, power source 47 may include power supply circuitry to produce appropriate operating voltages and/or currents.

The stimulation energy generated by therapy delivery module 40 may be formulated as neurostimulation energy, e.g., for treatment of any of a variety of neurological disorders, or disorders influenced by patient neurological response. The signals may be delivered from therapy delivery module 40 to various, selected combinations of electrodes 7 via a switch matrix and conductors carried by leads 14 and electrically coupled to respective electrodes 7.

Processor 42 may include one or more microprocessors, controllers, digital signal processors (DSPs), application specific integrated circuits (ASICs), field programmable gate arrays (FPGAs), discrete logic circuitry, or the like, or any combination thereof. Processor 42 controls the implantable signal generator within therapy delivery module 40 to deliver neurostimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the neurostimulation signals via selected subsets of electrodes 7 with selected polarities. For example, electrodes 7 may be combined in various bipolar or multi-polar combinations, including combinations of electrodes on the same lead or different leads, to deliver stimulation energy to selected sites, such as nerve sites adjacent an occipital nerve, spinal column, pelvic floor nerve sites, or cranial nerve sites. Electrodes 7 may also be combined in various bipolar or multi-polar combinations to deliver stimulation energy to selected sites, such as nerve sites adjacent the spinal column, pelvic floor nerve sites, or cranial nerve sites.

Processor 42 may also control therapy delivery module 40 to deliver each signal according to a different program, thereby interleaving programs to simultaneously treat different symptoms or provide a combined therapeutic effect. For example, in addition to treatment of one symptom such as migraine headaches, electrical stimulator 12 may be configured to deliver neurostimulation therapy to treat other symptoms such as back pain. In such an embodiment, electrodes 7A of paddle 17A may be positioned to deliver stimulation therapy for treating one symptom, and electrodes 7B of paddle 17B may be positioned to deliver stimulation therapy for treatment of another symptom.

Memory 44 of electrical stimulator 12 may include any volatile or non-volatile media, such as a RAM, ROM, NVRAM, EEPROM, flash memory, and the like. In some embodiments, memory 44 of electrical stimulator 12 may store multiple sets of stimulation parameters that are available to be selected by patient 16 via patient programmer 28 (FIG. 1) or a clinician via clinician programmer 26 (FIG. 1) for delivery of neurostimulation therapy. For example, memory 44 may store stimulation parameters transmitted by clinician programmer 26 (FIG. 1). Memory 44 also stores program instructions that, when executed by processor 42, cause electrical stimulator 12 to deliver neurostimulation therapy according to selected programs or program groups. Accordingly, computer-readable media storing instructions may be provided to cause processor 42 to provide functionality as described herein.

Processor 42 may control telemetry module 46 to exchange information with an external programmer, such as clinician programmer 26 and/or patient programmer 28 (FIG. 1), by wireless telemetry. In addition, in some embodiments, telemetry module 46 supports wireless communication with one or more wireless sensors that sense physiological signals and transmit the signals to electrical stimulator 12.

Figure 3A:
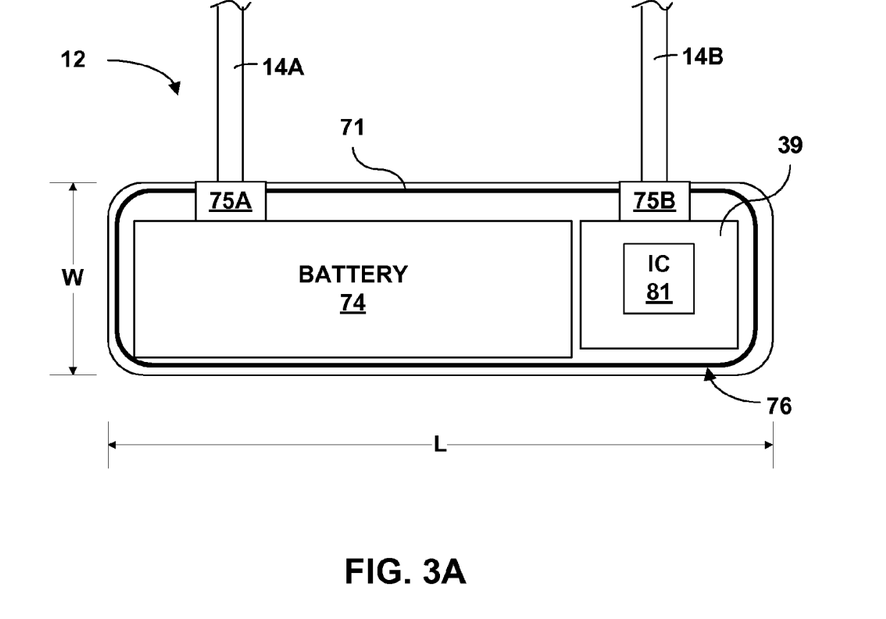
FIGS. 3A and 3B respectively illustrate a top view and a side view of an electrical stimulator.
Figure 3B:
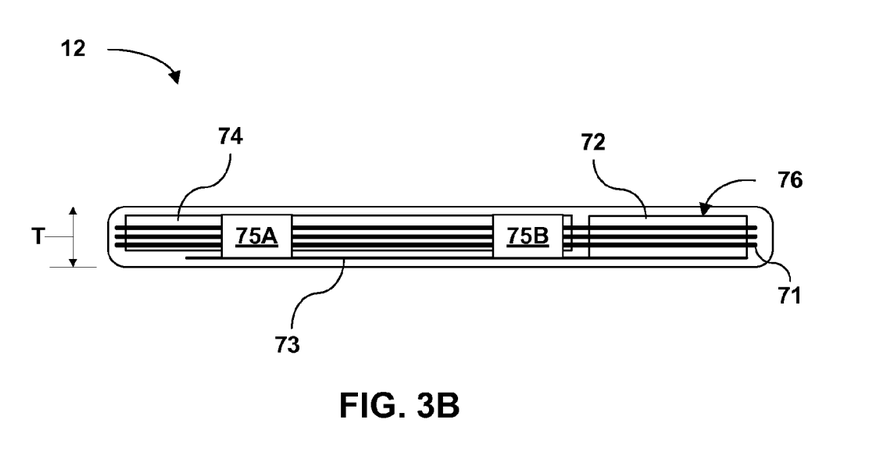

FIG. 3A illustrates a top view of an example of electrical stimulator 12. FIG. 3B illustrates a side view of electrical stimulator 12. Electrical stimulator 12 may be subcutaneously implanted at a stimulation site adjacent a neuralgic region of a patient. In particular, electrical stimulator 12 may be subcutaneously implanted at the back of the neck of the patient, as in the example of FIG. 1A.

As shown in FIGS. 3A-3B, electrical stimulator 12 comprises a housing 71 that may contain a control module 39, a battery 74, and a telemetry and/or recharge coil 76 encircling an inner perimeter of housing 71. Electrical stimulator 12 may also include flexible circuit 73 and connector blocks 75A and 75B (collectively "connector blocks 75"). Connector blocks 75 each include a connection port to accept one of leads 14. In other embodiments, leads 14 may be permanently attached to connector blocks 75. Connector blocks 75 may be separated by a distance of at least one-third of the length of housing 71. For example, Connector blocks 75 may separated by a distance of at least one-half, two-thirds or three-fourths of the length of housing 71. The combination of flexible circuit 73 and connector blocks 75 provide an electrical connection path, e.g., via copper traces, between control module 39 and leads 14. As one example, components of control module 39 may be mounted directly to flexible circuit 73.

Coil 76 may serve as an inductive power interface to recharge battery 54, as well as a telemetry coil for wireless communication with an external programmer, e.g., as part of telemetry module 46. In some embodiments, coil 76 may encircle control module 39, battery 74, or both. Battery 74 may form part of power source 47. Coil 76 inductively receives energy from an external recharging unit (not illustrated) through the skin of the patient to recharge battery 74.

Coil 76 may be formed of insulated windings of copper or another highly conductive material. Electrical stimulator 12 also includes two leads 14 to provide stimulation to the neuralgic region of the patient. Control module 39 receives power from battery 74 to drive the electrodes on leads 14 according to a stimulation program included in control module 39. In various embodiments, the leads 14 may be paddle, axial or subcutaneous leads.

Housing 71 conforms to a substantially rectangular form factor, but may include rounded corners and/or a curved major surface to facilitate implantation inferior to the inion of a patient. For example, such a configuration may reduce the likelihood of necrosis to a patient's scalp adjacent the implant site.

Generally, the larger electrical stimulator 12 is, the higher capacity battery electrical stimulator 12 can hold. A higher capacity battery extends the operational time allowed between recharging. However, smaller devices may allow easier implantation, improved cosmetic appearance and patient comfort. Housing 71 may conform to a miniaturized form factor with a low profile in order to fit directly adjacent the neuralgic region of the patient. The housing may have a volume between approximately 0.5 cubic centimeters (cc) and 5 cc. For example, the housing may have a volume equal to or greater than approximately 1.5 cc and less than or equal to 2.5 cc. An aspect ratio of the length L of the housing to the width W of the housing may be between approximately 1.5:1 and 2:1. In other embodiments, the aspect ratio of the length L of the housing to the width W of the housing may be about 1:1. The width W may be between about 20 mm (0.8 inches) and 76 mm (3.0 inches). For example, the width W may be between about 10 mm (0.4 inches) and 51 mm (2.0 inches). The thickness T may be between about 3 mm (0.12 inches) and about 10 mm (0.40 inches). For example, the thickness T may be between about 4 mm (0.16 inches) and about 5 mm (0.20 inches).

Battery 74 may comprise a rechargeable battery with a capacity of at least 20 milliamp-hours, more preferably at least 25 milliamp-hours, and still more preferably at least 30 milliamp-hours. In some embodiments, battery 74 may comprise a lithium ion rechargeable battery. Battery 74 may conform to a miniaturized form factor to fit within housing 71. Battery 74 may comprise a length of less than or equal to about 25 mm (1.0 inches), a width of less than or equal to about 12.7 mm (0.50 inches), and a thickness of less than or equal to about 3.3 mm (0.13 inches). Battery 74 may conform to one of a variety of designs.

Electrical stimulator 12 may be over-discharge protected. However, since battery 74 conforms to an extremely small form factor, the over-discharge protection may be difficult to realize using traditional approaches, such as extra battery capacity. Therefore, electrical stimulator 12 may include a switch to disconnect battery 74 from the load when a predetermined voltage is reached. In other cases, battery 74 may comprise an over-discharge tolerant battery.

Control module 39 may also conform to a miniaturized form factor to fit within housing 71. Control module 39 may comprise a length of less than or equal to about 6.5 mm (0.256 inches), a width of less than or equal to about 9.4 mm (0.37 inches), and a thickness of less than or equal to about 3.6 mm (0.14 inches). Control module 39 also couple to coil 76, which may operate as both a recharge coil and a telemetry coil. Control module 39 may receive energy via recharge coil 76 to recharge battery 74. Control module 39 may also receive stimulation programs and other instructions from the patient, the physician, or the clinician via telemetry coil 76.

Control module 39 may comprise an integrated circuit (IC) 81 designed to minimize the number of components within electrical stimulator 12. For example, IC 81 may perform the functions of control module 39 (FIG. 2) and/or other functions. In some implementations, IC 81 may be formed from an ASIC. IC 81 may be designed using an 0.8 micron process in an effort to reduce the overall size and profile of electrical stimulator 12. With sufficient processing power, IC 81 may have a footprint of about 5.2 mm (0.204 inches) by 5.2 mm and a thickness of about 0.46 mm (0.018 inches).

Figure 4:
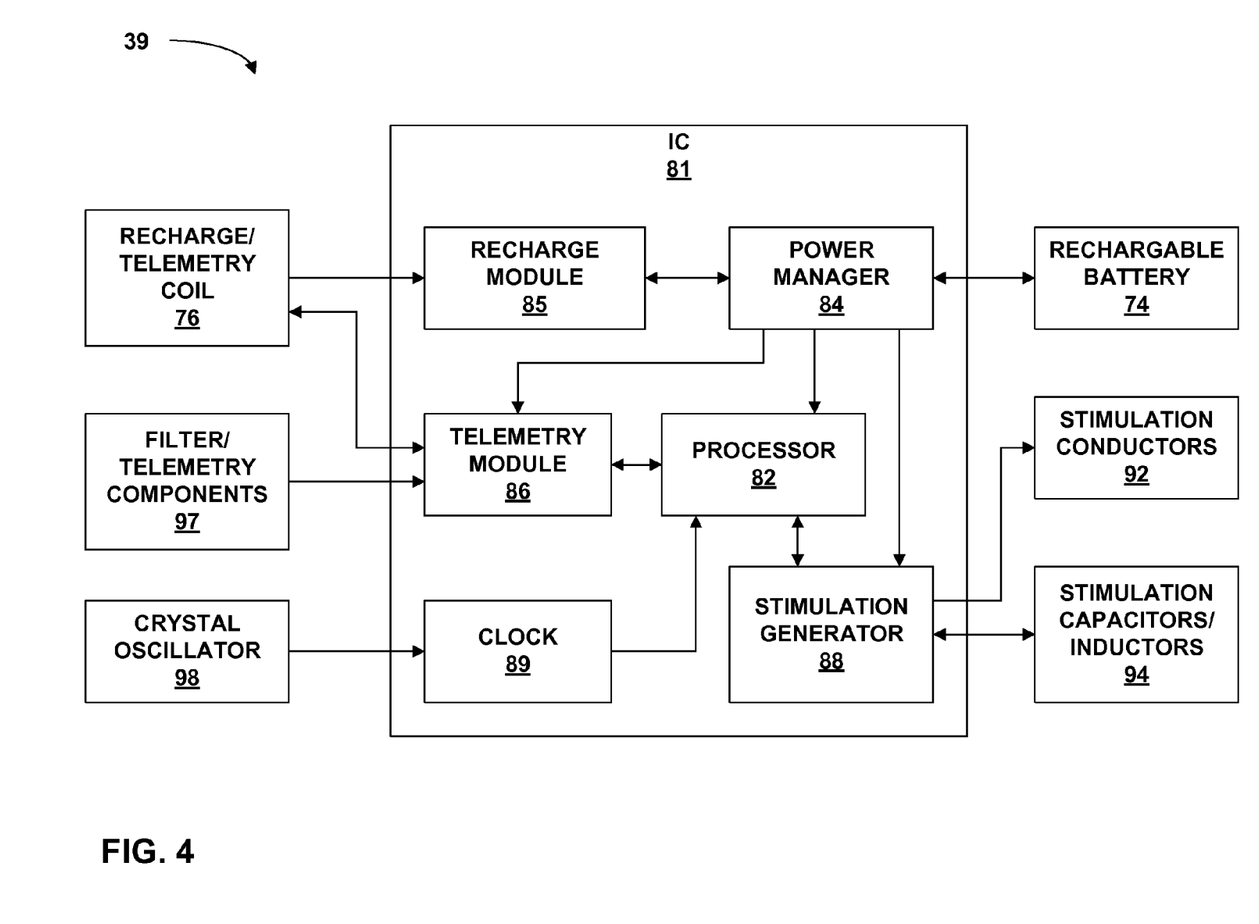
FIG. 4 is a block diagram illustrating an exemplary control module included in an on-site electrical stimulator for the treatment of a patient such as the electrical stimulator of FIG. 2.

FIG. 4 is a block diagram illustrating an example control module 39, which may be similar to the control module of FIG. 2. Control module 39 comprises IC 81, stimulation capacitors and inductors 94, filter and telemetry components 97, and a crystal oscillator 98 positioned on a substrate board. One or more memory devices, such as memory 44, also may be provided. The substrate board may comprise a minimal number of layers, e.g. four layers or less, and comprise a thickness equal to or less than about 0.4 mm (0.014 inches). In one example, the substrate board may be a flexible circuit as shown in FIGS. 3A and 3B.

Control module 39 couples to a rechargeable battery 74, which may form part of power source 47, conductors 92 that connect to one or more stimulation electrodes of the electrical stimulator, and a recharge and telemetry coil 76. As previously mentioned, coil 76 may operate as both a recharge coil and a telemetry coil. In some cases, as described above, coil 76 may encircle control module 39. IC 81 includes a processor 82, a power manager 84, a recharge module 85, a telemetry coil 76, a stimulation generator 88, and a clock 89.

Power manager 84 couples to rechargeable battery 74 to provide power to processor 82, recharge module 85, telemetry coil 76, and stimulation generator 88. Recharge module 85 couples to recharge and telemetry coil 76 and receives power via coil 76 to recharge battery 74. Telemetry coil 76 also couples to recharge and telemetry coil 76 and receives stimulation programs and other instructions from a programmer operated by the patient or physician via coil 76. Filter, power management, telemetry components 97 couple to telemetry coil 76 to support reliable wireless communication. Examples of filter, power management and telemetry components 97 include a telemetry tank capacitor, voltage regulation filters, power supply filters, and battery bypass capacitors. Telemetry coil 76 then provides the received stimulation programs to processor 82, which stores the programs in memory (not shown).

Crystal oscillator 98 is coupled to clock 89, which clocks processor 82 to run the stimulation programs. Processor 82 directs stimulation generator 88 to provide stimulation to the electrodes of the electrical stimulator via stimulation conductors 49. Processor 82 directs stimulation generator 88 according to the stimulation programs received from telemetry coil 76 and the clock cycle received from clock 89. Stimulation generator 88 is coupled to stimulation capacitors and inductors 94, which include capacitors to store stimulation pulses.

As an example, a stimulation program may instruct stimulation generator 88 to generate a stimulation waveform having an amplitude of about 1 to 40 milliamps, or even 6 to 10, a frequency of about 10 to 500 Hz, and even 20 to 200 Hz, and a duration of about a few seconds to several minutes. The stimulation waveform may have a substantially square or spiked waveform. In some embodiments, a neurostimulation waveform may have a duty cycle in a range of about 15 to 25 percent, i.e., "on" for 15 to 25 percent of the time, and even 20 percent of the time.

In other embodiments, a stimulation program may instruct stimulation generator 88 to generate a stimulation pulse; for example, a duration of about 20 to 800 microseconds, and even 80 to 120 microseconds may be used.

Figure 5:
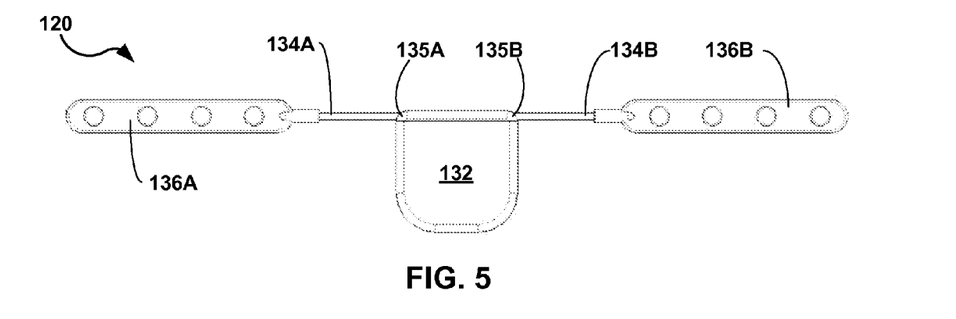
FIG. 5 illustrates a therapy system including an electrical stimulator with a different shape than the electrical stimulator shown in FIGS. 1A and 1C-1E.

FIG. 5 illustrates therapy system 120, which includes electrical stimulator 132 and paddle leads 134A, 134B (collectively referred to as "leads 134"). Therapy system 120 may be substantially similar to therapy system 10. In contrast to electrical stimulator 12 (FIGS. 1A and 1C-1E), however, electrical stimulator 132 has an about square shape such that its length and width dimensions are similar. For example, electrical stimulator 132 may have a width and a length of between about 0.45 inches to 1.6 inches and a thickness of about 0.120 inches to 0.240 inches. The shape may be rounded at the corners. Other features of therapy system 120 are similar to therapy system 10 (FIGS. 1A and 1C-1E). For brevity, these features are not described in detail with respect to therapy system 120, and in some instances such features are not described at all with respect to therapy system 120.

Electrical stimulator 132 includes two connector blocks, each having one of connection ports 135A, 135B (collectively referred to as "connection ports 135"). Connection ports 135 provide an electrical connection to leads 134. For example, connection ports 135 may provide a press-fit with a proximal end of one of leads 134. Connection ports 135 may include electrical contacts that mate with corresponding electrodes on a proximal end of one of leads 134. In other embodiments, leads 134 may be permanently attached to separate connector blocks within electrical stimulator 132. Connection ports 135 are separated by at least a third of the length of the housing of electrical stimulator 132. In fact, as shown in FIG. 5, connection ports 135 are located on opposing surfaces of the housing of electrical stimulator 132 such that the connector blocks are oriented in opposite directions and separated by the entire width of the housing of electrical stimulator 132.

Leads 134 include paddle electrode sets 136A, 136B to deliver stimulation therapy to a patient. Like leads 14, lead 134 are flexible to conform to the skull of a patient. For example, therapy system 120 may be implanted beneath the scalp and inferior to the inion of a patient to deliver stimulation therapy to at least one of an occipital nerve and a branch of the occipital nerve.

Figure 6:
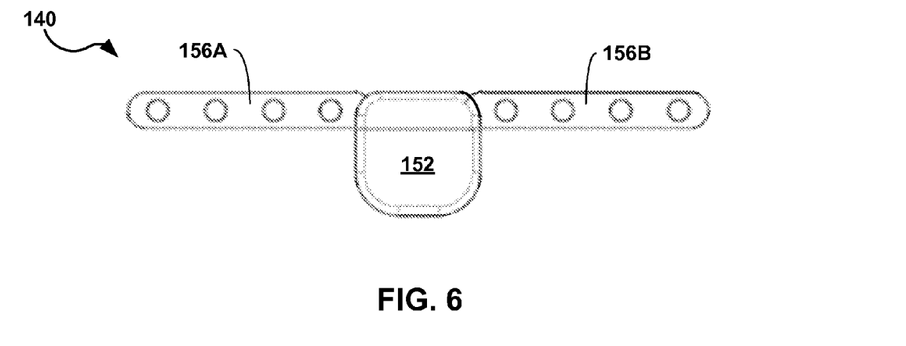
FIG. 6 illustrates a therapy system including an electrical stimulator having a housing with two paddle electrode sets coupled directly to the housing.

FIG. 6 illustrates therapy system 140, which includes electrical stimulator 152 and paddle electrode sets 156A, 156B (collectively referred to as "paddle electrode sets 156"). Electrical stimulator 152 has an about square shape such that its length and width dimensions are similar. For example, electrical stimulator 152 may have a width of between about 0.45 inches to 1.6 inches, a length of between about 0.45 inches to 1.6 inches and a thickness of about 0.120 inches to 0.240 inches. Other form factors are also possible.

In contrast to therapy system 10 (FIGS. 1A and 1C-1E) paddle electrode sets 156 may be hardwired to electrical stimulator 152 and are not part of leads. For example, paddle electrode sets 156 may be electrically coupled to a circuit of electrical stimulator 152 via solder connections, set screws or other techniques. Other features of therapy system 140 are similar to therapy system 10 (FIGS. 1A and 1C-1E). For brevity, these features are not described in detail with respect to therapy system 140, and in some instances such features are not described at all with respect to therapy system 140.

Electrical stimulator 152 includes a stimulation generator to deliver stimulation therapy to a patient via paddle electrode sets 156. For example, therapy system 120 may be implanted beneath the scalp and inferior to the inion of a patient to deliver stimulation therapy to at least one of an occipital nerve and a branch of the occipital nerve. Once therapy system 140 is implanted electrodes sets 156 may be adjacent to target stimulation sites, such as stimulations sites 18, 19 (FIG. 1A).

Figure 7:
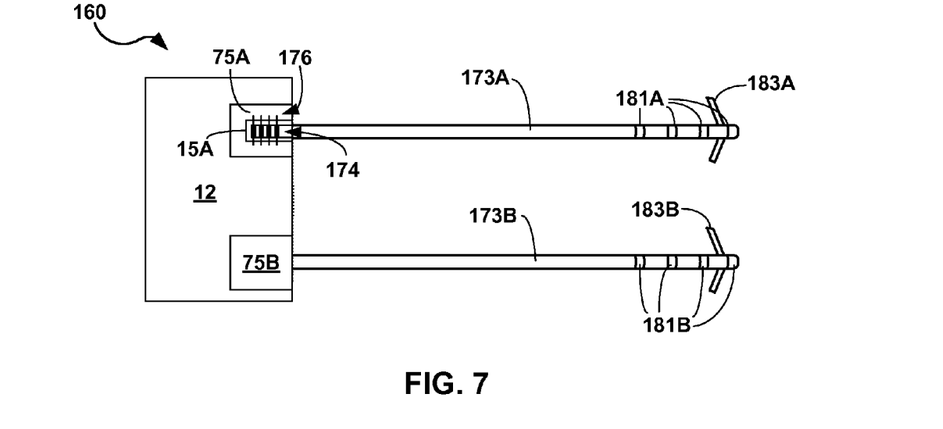
FIG. 7 illustrates a therapy system including an electrical stimulator coupled to two axial leads.

FIG. 7 illustrates therapy system 160, which includes electrical stimulator 12 and axial leads 173A, 173B (collectively referred to as "leads 173"). As also shown in FIGS. 3A-3B, electrical stimulator 12 includes connector blocks 75. Connector block 75A is shown in detail, but the details shown with respect connector block 75A are also attributable connector block 75B. Specifically, connector block 75A includes connection port 15A, which receives a proximal end of lead 173A. Connection port 15A includes a set of terminals 176 at different axial positions that mate with contacts 174 at different axial positions at the proximal end of lead 173A. The connection between lead 173A and connection port 15A includes fluid seals to prevent undesirable electrical discharge. Lead 173A may be removed from connection port 15A by a clinician if desired. For example, the removable connection may be a pressure or snap-fit, e.g., with a spring contacts.

Axial leads 173 provide an alternative to paddle leads 14 (FIG. 1A). Axial leads 173 include ring electrodes sets 181A, 181B (collectively referred to as "electrodes 181") disposed the distal ends of leads 173. The configuration, type, and number of electrodes 181 illustrated in FIG. 7 are merely exemplary. In some embodiments, electrodes 181 may be ring electrodes. In other embodiments, electrodes 181 may be segmented or partial ring electrodes, each of which extends along an arc less than 360 degrees (e.g., 90-120 degrees) around the periphery of leads 173.

Leads 173 may include fixation elements 183A, 183B (collectively referred to as "fixation elements 183"). Fixation elements 183 may help locally fix electrodes 181 proximate to target stimulation sites 18, 19 (FIG. 1). Fixation elements 183 may be expanded or activated by any suitable means. In some embodiments, fixation elements 183 may be restrained or otherwise prevented from premature fixation by a lead introducer, sheath, or other mechanism, prior to introduction into a patient. Upon implantation, fixation elements 183 may be expanded or activated by active or passive means. Fixation elements 183 may each be any suitable actively or passively deployed fixation element that helps prevent migration of leads 173 when leads 173 are implanted in a patient, such as, but not limited to, one or more barbs, hooks, wire-like elements, adhesives (e.g., surgical adhesives), balloon-like fixation elements, tissue receiving cavities, pinning fixation elements, collapsible or expandable fixation structures, and so forth. In addition, fixation elements 183 may be formed in situ (i.e., after leads 173 are implanted in patient 16), such as by delivering a solidifying material (e.g., an adhesive or a hardenable structure material) to one or more exit ports along one or more surface of leads 173 to form fixation elements that extend from lead 32 and/or 33 to engage with surrounding tissue. Fixation elements 183 may be composed of any suitable biocompatible material, including, but not limited to, polymers, titanium, stainless steel, Nitinol, other shape memory materials, hydrogel or combinations thereof.

In some embodiments, fixation elements 183 are attached directly to leads 173. However, in other embodiments, fixation elements 183 may not be attached directly to leads 173, but may be carried by another apparatus that is attached to the leads 173, such as a sleeve or mounting band.

Figure 8A:
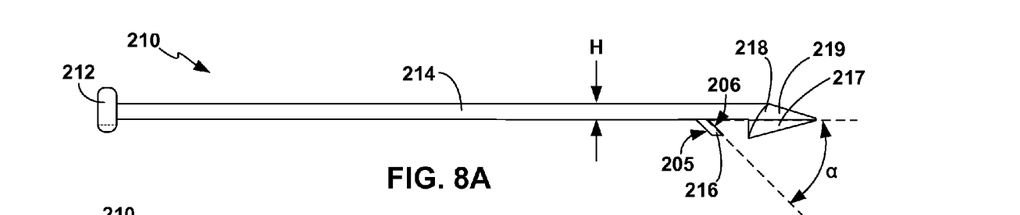
FIGS. 8A-8B illustrate a medical lead introducer including a blunt dissection element and a tab configured to engage a distal end of a medical lead.
Figure 8B:
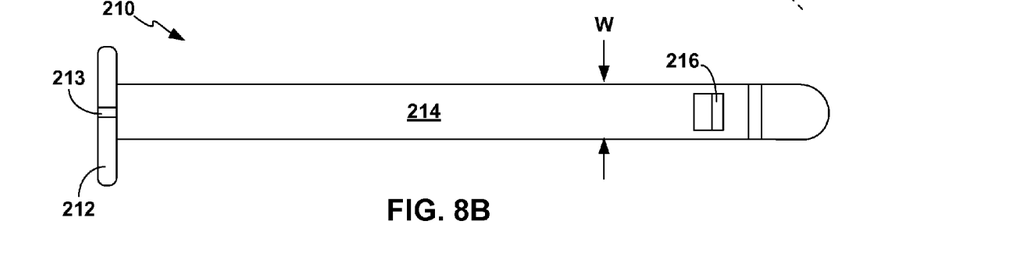
Figure 9A:
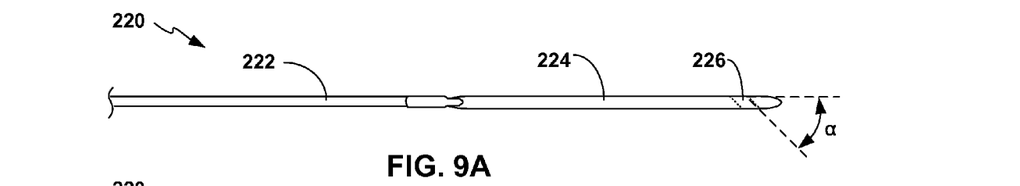
FIGS. 9A-9B illustrate a medical lead configured for insertion within a patient using the medical lead introducer of FIGS. 8A-8B.
Figure 9B:
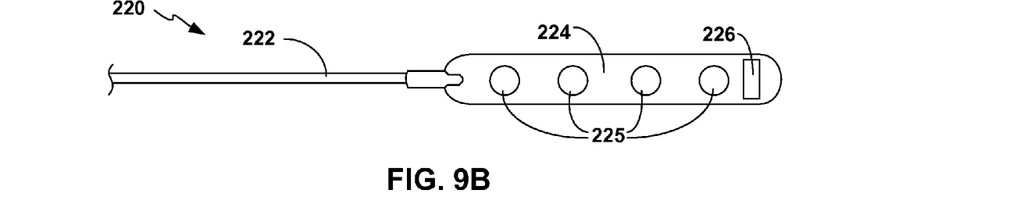
Figure 10:
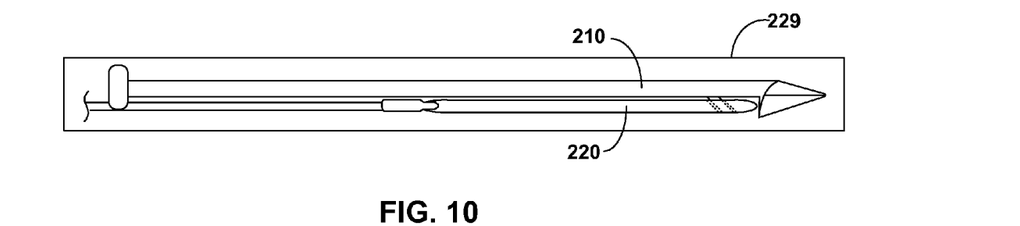
FIG. 10 illustrates a kit including a medical lead and a medical lead introducer packaged in a sterile container.

FIGS. 8A-8B illustrate a medical lead introducer 210 for use in deploying an implantable medical lead, which includes blunt dissection element 218. FIGS. 9A-9B illustrate medical lead 220, which is configured for insertion within a patient using medical lead introducer 210. FIG. 10 illustrates a kit including medical lead 220 and medical lead introducer 210 packaged in sterile container 229. Medical lead introducer 210 is configured such that one side of medical lead 220 is exposed to patient tissue during a lead introduction procedure. Lead introducer 210 facilitates the positioning of medical lead 220 proximate a target tissue site within a patient simultaneously with the blunt dissection of patient tissue. For example, medical lead 220 may be implanted with medical lead introducer 210 in patient 16 in place of one or both of leads 14 (FIG. 1A).

In the example of FIGS. 9A and 9B, medical lead 220 is a paddle lead including one or more electrodes 225 on paddle 224 to deliver stimulation therapy to therapy region within a patient. Medical lead 220 also includes lead body 222, which includes insulated conductors in electrical communication with electrodes 225. A proximal end of medical lead 220 is configured to be electrically and mechanically connected to an electrical stimulation therapy delivery device to deliver stimulation therapy to a patient via electrodes 225. Electrodes 225 may also be used as sensing electrodes to sense one or patient parameters, including, but not limited to, patient parameters related to a patient response to stimulation. In addition medical lead 220 may include fluoroscopic elements to allow a clinician to more easily determine an orientation and position of medical lead 220 using fluoroscopy during implantation.

Medical lead introducer 210 is configured to implant medical lead 220 proximate a target tissue site within a patient. Medical lead introducer 210 includes shank 214 and blunt dissection element 218, which is fixed to the distal end of shank 214. Lead introducer 210 includes handle 212 on the proximal end of lead introducer 210. Handle 212 allows a clinician to apply a significant force to lead introducer 210 in order to tunnel through tissue of a patient using blunt dissection element 218. Generally, the profile of medical lead introducer 210 should be kept to a minimum to limit the size of a tunnel created within a patient when implanting medical lead 220 with medical lead introducer 210. Limiting the size of the tunnel may not only reduce patient trauma associated within implantation, but may also reduce lead migration after implantation.

Shank 214 has a rectangular cross section, although in other examples different cross-sectional shapes may also used. For example, the width W of shank 214 may be at least three times greater than the height H of shank 214. Generally, the width of shank 214 may be about equal to the width of paddle 224. The cross section of medical lead introducer 210 may cause shank 214 to have greater flexibility about its height and limited side-to-side flexibility. The uneven flexibility provided by shank 214 may improve the steerablity of lead introducer 210 when tunneling through tissue of a patient by substantially constraining the bending of shank 214 to be within a single plane. In different examples, lead introducer 210 may be may substantially stiff such that it will not bend during a blunt dissection procedure.

In the example of FIGS. 8A and 8B, medical lead introducer 210 also includes tab 216, which extends from shank 214. Tab 216 is configured to engage through-hole 226 of medical lead 220 to hold medical lead 220 during a lead introduction procedure. In this manner, tab 216 serves as a carrier structure, whereas through-hole 226 serves as a mating carrier structure. Through-hole 226 is located at the distal end of medical lead 220 in paddle 226. In other examples, paddle 226 may include a detent as a mating carrier structure to be engaged by tab 216 in place of through-hole 226. In other examples, carrier structures may include additional tabs similar to tab 216 to engage multiple depressions on a medical lead.

Tab 216 extends at a forward angle α relative to the insertion direction of lead introducer 210. Likewise, through-hole 226 passes through paddle 224 at about the same angle α. As examples, the angle α may be between 10 and 80 degrees, between 30 and 60 degrees, or may be about 45 degrees. In some embodiments, distal surface 6 of tab 216 may be at different angle as compared to proximal surface 5 relative to the insertion direction of lead introducer 210. For example, distal surface 6 may be at a larger angle than proximal surface 5 of lead introducer 210. This may increase the strength of tab 216 for a given angle of the proximal surface 5 as a smaller angle of the proximal surface 5 may make it easier to release lead 220 from lead introducer 210. As examples, distal surface 6 may be at an angle of between 5 and 75 degrees greater than the angle of proximal surface 5, at an angle of between 15 and 60 degrees greater than the angle of proximal surface 5 or at an angle of about 20 degrees greater than the angle of proximal surface 5.

Detent 213 also may be provided to help secure medical lead 220 during a lead introduction procedure. Detent 213 is located on handle 212, and is configured to secure lead body 222 as shown in FIG. 10. For example, detent 213 may provide a snap-fit interface with lead body 222. This snap-fit interface may assist in keeping lead body 222 in line with lead introducer tool 210 and may also hold through-hole 226 in paddle 224 of lead 220 in engagement with tab 216.

Lead introducer 210 is inserted as part of an assembly also including lead 220 into the tissue of a patient. Tab 216 extends from shank 214 and is angled towards the distal end of lead introducer 210, i.e., towards blunt dissection element 218. Likewise, through-hole 226 has a similar angled configuration to mate with tab 216. As a clinician forces lead introducer 210 through patient tissue, friction of patient tissue pulls on lead 220 including paddle 224. The angled configuration of tab 216 and through-hole 226 holds tab 216 in engagement with paddle 224. The clinician continues to force introducer 210 in a forward direction through patient tissue until electrodes 225 are positioned adjacent a target tissue site.

After advancing lead 220 to the desired location, the clinician withdraws introducer 210. The angled configuration of tab 216 and through-hole 226 allows tab 61 to withdraw from through-hole 226 and introducer 210 to slide out over lead 220 without significantly disturbing placement of lead 220. An important feature of lead introducer 210 is that it does not encompass lead 220 during lead placement within a patient, i.e., at least one side of lead 220 is exposed to patient tissue during implantation. This allows lead 220 to be implanted simultaneously while tunneling through patient tissue. It also facilitates implantation of leads that are permanently fixed to a stimulation device since the introducer does not need to slide off the proximate end of the lead. While the specific example of tab 216 and through-hole 226 are suitable as a carrier structure and mating carrier structure respectively, many other structures may also be used for a lead introducer that does not encompass the lead during lead placement within a patient.

Blunt dissection element 218 may have a tapered tip to facilitate blunt dissection through tissue of a patient. As best shown in FIG. 10, blunt dissection element 218 has a frontal area that extends beyond a frontal area of shank 214. As referred to herein, a frontal area is the two-dimensional area in the geometric plane that is perpendicular to the insertion direction. In this manner, blunt dissection element 218 provides a frontal area that shields medical lead 220 when medical lead 220 is held by medical lead introducer 210 during a lead introduction procedure. Because blunt dissection element 218 is not centered on the distal end of shank 214, the insertion force applied by a clinician to handle 212 does not inherently balance with the tunneling force applied to blunt dissection element 218 by tissue of a patient. Instead, the off-center position of shank 214 relative to blunt dissection element 218 biases lead introducer 210 down in the direction of lead 210. For this reason, blunt dissection element 218 is asymmetrical to balance the insertion force against the blunt dissection force. This limits bending of the medical lead introducer resulting from the combination of the insertion force and the blunt dissection force. For example, blunt dissection element 218 may defined a surface 217 that is proximate to the side of shank 216 that includes tab 216 and surface 219, which opposes the first surface 217. In order to balance the insertion force against the blunt dissection force, the frontal area of surface 217 may be greater than the frontal area of the surface 219.

Medical lead introducer 210 may be made of any material suitable for facilitating implantation of a medical lead. In addition, medical lead introducer 210 may include fluoroscopic elements to allow a clinician to more easily determine an orientation and position of the lead introducer 210 using fluoroscopy during implantation of a medical lead. For example, medical lead introducer 210 may be made from stainless steel, titanium, polyester, polyurethane, silicone, and/or plastic, or other biocompatible materials. In some instances, all or a portion of lead introducer 210 may be coated, e.g., with Polytetrafluoroethylene (PTFE), to reduce friction with a patient's tissue during a lead introduction procedure.

As shown in FIG. 10, medical lead introducer 210 may come packaged as a kit including medical lead 220 packaged in sterile container 229. As examples, sterile container 229 may be a flexible plastic enclosure, foil packaging or other suitable sterile container. In such an example, lead introducer 210 may be disposable after implantation of lead 220. In other examples, lead introducer 210 may be reused to implant multiple leads.

Embodiments of the invention may provide one or more advantages. For example, in embodiments where the stimulation therapy system including an electrical stimulator and leads is sized to be located adjacent the occipital region of a patient, embodiments of the invention allow for stimulation therapy system including an electrical stimulator and leads to be implanted via a single incision. Implanting both the electrical stimulator and leads via a single incision may reduce patient discomfort during recovery from the implantation procedure as well as reduce surgery time compared to systems in which the electrical stimulator is not located adjacent to the target stimulation region of a patient.

Furthermore, locating the electrical stimulator adjacent the target stimulation region of a patient, allows for relatively short leads. Short leads can limit lead migration due to patient movement. Short leads allow have a lower resistance for a given diameter electrical conductor, which can improve the efficiency to reduce power consumption.

Furthermore, because the electrical stimulator and leads are implanted via a single incision, the invention allows embodiments in which the leads are permanently attached to the electrical stimulator. Permanently attached leads may provide for therapy systems that are more reliable because there can be a permanent seal between the permanently attached leads may provide therapy systems with reduced manufacturing cost compared to systems with detachable leads.

Various embodiments of the invention have been described. The foregoing description of the exemplary embodiments of the invention has been presented for the purposes of illustration and description. They are not intended to be exhaustive or to limit the invention to the precise forms disclosed. Many modifications and variations are possible in light of the above teaching. For example, although application of various embodiments of the invention to occipital neuralgia has been described for purposes of illustration, the invention may be applied to treat a variety of disorders. The scope of the invention is not limited with this detailed description, but rather by the claims. These and other embodiments are within the scope of the following claims.

The invention claimed is:

1. An implantable medical device comprising:
   one or more electrical stimulation generators;
   a housing that contains the one or more electrical stimulation generators;
   a first medical lead no greater than about 6 inches in length; and
   a second medical lead no greater than about 6 inches in length,
   wherein the housing includes a first connector block forming a first connection port with a first terminal that electrically connects the first medical lead to at least one of the one or more electrical stimulation generators, and a second connector block forming a second connection port with a second terminal that electrically connects the second medical lead to at least one of the one or more electrical stimulation generators,
   wherein the first connector block is not in direct contact with the second connector block, and
   wherein the one or more electrical stimulation generators are configured to deliver electrical stimulation to a patient via each of the first medical lead and the second medical lead.

2. The device of claim 1,
   wherein the housing has a width and a length that are each greater than a thickness of the housing, and
   wherein the connector blocks are located at least a third of the length of the housing apart from one another.

3. The device of claim 1, wherein a major surface of the housing is curved to accommodate implantation inferior to the external occipital protuberance.

4. The device of claim 1, wherein the housing has a volume between about 0.5 cubic centimeters (cc) and 5 cc.

5. The device of claim 1,
   wherein the housing has a width and a length that are each greater than a thickness of the housing, and
   wherein an aspect ratio of a length of the housing to a width of the housing is between about 1.5:1 and 2:1.

6. The device of claim 1,
   wherein the housing has a width and a length that are each greater than a thickness of the housing, and
   wherein the connector blocks are located on at least one surface of the housing defined by the thickness.

7. The device of claim 6, wherein the connector blocks are oriented in about the same direction.

8. The device of claim 6, the connector blocks are oriented in about opposite directions.

9. The device of claim 1, wherein the connector blocks are separated by between about 0.5 inches and about 1.3 inches.

10. The device of claim 1, wherein the medical leads include a paddle lead.

11. The device of claim 1, wherein the one or more electrical stimulation generators are configured to deliver electrical stimulation selected to alleviate occipital neuralgia when applied to at least one of an occipital nerve and a branch of the occipital nerve.

12. An electrical stimulation system comprising:
an electrical stimulator comprising:
- a housing having a width and a length that are each greater than a thickness of the housing,
- one or more stimulation generators within the housing, and
- at least two connector blocks, wherein each connector block includes a connection port with a terminal that accepts a medical lead; and at least two medical leads extending from the housing and electrically coupled to the stimulation generator via the connection ports and terminals of the connector blocks, wherein two of the medical leads exit the housing at separate locations, wherein the separate locations are separated by at least a third of the length of the housing, wherein each of the at least two medical leads are no greater than about 6 inches in length, and wherein the one or more stimulation generators are configured to deliver electrical stimulation to a patient via each of the first medical lead and the second medical lead.

13. The system of claim 12, wherein a major surface of the housing is curved to accommodate implantation inferior to the external occipital protuberance.

14. The system of claim 12, wherein the housing has a volume equal to or greater than 1.5 cc and less than or equal to 2.5 cc.

15. The system of claim 12, wherein an aspect ratio of a length of the housing to a width of the housing is between 1.5:1 and 2:1.

16. The system of claim 12, wherein two of the medical leads connect to the housing on opposing external surfaces of the housing.

17. The system of claim 12, wherein the one or more stimulation generators are configured to deliver electrical stimulation selected to alleviate occipital neuralgia when applied to at least one of a trigeminal nerve, a greater occipital nerve, a lesser occipital nerve, a third occipital nerve, or a suboccipital nerve.

18. The system of claim 12, wherein the at least two medical leads are permanently coupled to the housing and the stimulation generator.

19. The system of claim 12, wherein the one or more stimulation generators are configured to deliver electrical stimulation selected to treat at least one of head pain, neck pain, neck tension, facial pain, facial tension, and pain or tension caused by occipital neuralgia.

20. The system of claim 12, wherein the medical leads include a paddle lead.

21. The system of claim 12, wherein the medical leads include an axial lead.

22. The system of claim 12, wherein the separate locations are separated by between about 0.5 inches and about 1.3 inches.

23. The device of claim 1, wherein the medical leads include an axial lead.

24. A method for implanting an electrical stimulation system in a patient comprising:
making an incision in the skin of a patient inferior to the inion of the patient,
wherein the electrical stimulation system comprises:
an electrical stimulator comprising:
- a housing having a width and a length that are each greater than a thickness of the housing,
- one or more stimulation generators within the housing, and
- at least two connector blocks, wherein each connector block includes a connection port with a terminal that accepts a medical lead, and at least two medical leads extending from the housing and electrically coupled to the stimulation generator via the connection ports and terminals of the connector blocks, wherein two of the medical leads exit the housing at separate locations, wherein the separate locations are separated by at least a third of the length of the housing, wherein each of the at least two medical leads are no greater than about 6 inches in length, and
wherein the one or more stimulation generators are configured to deliver electrical stimulation to a patient via each of the first medical lead and the second medical lead;

tunneling lateral paths under the skin laterally both to the right and to the left of the incision, wherein the paths are sized to accept the medical leads of the electrical stimulation system;

forming an inferior pocket under the skin inferior to the inion, wherein the pocket is sized to accept the housing of the electrical stimulator of the electrical stimulation system;

inserting the medical leads of the electrical stimulation system into the lateral paths;

inserting the housing into the inferior pocket; and
closing the incision.

25. The method of claim 24, further comprising delivering stimulation therapy with the implanted electrical stimulation system to treat at least one of head pain, neck pain, neck tension, facial pain, facial tension, and pain or tension caused by occipital neuralgia.

26. The method of claim 24, wherein the medical leads include at least one of a paddle lead and an axial lead.

27. The method of claim 24, wherein the medical leads each have a length of less than 6 inches.

28. The method of claim 24, wherein the electrical stimulator includes a battery within a housing and an inductive coil within the housing, wherein the method further comprises charging the battery via the inductive coil.

29. The method of claim 24, further comprising connecting the medical leads to the electrical stimulator.

* * * * *